United States Patent
Lelkes et al.

(10) Patent No.: US 8,048,446 B2
(45) Date of Patent: Nov. 1, 2011

(54) ELECTROSPUN BLENDS OF NATURAL AND SYNTHETIC POLYMER FIBERS AS TISSUE ENGINEERING SCAFFOLDS

(75) Inventors: Peter I. Lelkes, Cherry Hill, NJ (US); Mengyan Li, Philadelphia, PA (US); Mark Mondrinos, Philadelphia, PA (US); Frank Ko, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 126 days.

(21) Appl. No.: 11/431,484

(22) Filed: May 10, 2006

(65) Prior Publication Data

US 2006/0263417 A1    Nov. 23, 2006

Related U.S. Application Data

(60) Provisional application No. 60/679,309, filed on May 10, 2005.

(51) Int. Cl.
  *A61K 9/70* (2006.01)
  *A61K 38/39* (2006.01)
  *A61F 13/00* (2006.01)
  *C08G 63/08* (2006.01)

(52) U.S. Cl. ........ 424/443; 424/422; 530/353; 530/354; 528/272; 514/801

(58) Field of Classification Search .................. 424/443, 424/422; 530/353, 354; 528/272; 514/801
See application file for complete search history.

(56) References Cited

U.S. PATENT DOCUMENTS

| | | | |
|---|---|---|---|
| 4,829,000 A | 5/1989 | Kleinman et al. | |
| 5,554,389 A | 9/1996 | Badylak et al. | |
| 5,580,859 A | 12/1996 | Felgner et al. | |
| 5,787,567 A | 8/1998 | Miyazaki | |
| 5,908,777 A | 6/1999 | Lee et al. | |
| 5,910,488 A | 6/1999 | Nabel et al. | |
| 5,939,323 A | 8/1999 | Valentini et al. | |
| 6,099,567 A | 8/2000 | Badylak et al. | |
| 6,171,344 B1 | 1/2001 | Atala | |
| 6,306,424 B1 | 10/2001 | Vyakarnam et al. | |
| 6,379,710 B1 | 4/2002 | Badylak | |
| 6,398,819 B1 | 6/2002 | Bell | |
| 6,616,435 B2 | 9/2003 | Lee et al. | |
| 6,682,760 B2 | 1/2004 | Noff et al. | |
| 6,689,166 B2 | 2/2004 | Laurencin et al. | |
| 6,695,992 B2 | 2/2004 | Reneker | |
| 6,753,311 B2 | 6/2004 | Fertala et al. | |
| 6,753,454 B1 | 6/2004 | Smith et al. | |

(Continued)

FOREIGN PATENT DOCUMENTS

WO    WO 2004032713 A2 *    4/2004

(Continued)

OTHER PUBLICATIONS

Buijtenhuijs, P., et al. Tissue engineering of blood vessels: characterization of smooth-muscle cells for culturing on collagen-and-elastin-based scaffolds. Biotechnol Appl Biochem. 2004; 39:141-149, Abstract only.

(Continued)

*Primary Examiner* — Rosanne Kosson
(74) *Attorney, Agent, or Firm* — Riverside Law LLP (57) ABSTRACT

Non-woven fibrous scaffolds made by electrospinning from the synthetic biodegradable polymer such as, for example, poly(lactic-co-glycolic acid) (PLGA) and natural proteins, such as, for example, gelatin (denatured collagen) and elastin and a method of making thereof.

12 Claims, 4 Drawing Sheets

U.S. PATENT DOCUMENTS

| | | |
|---|---|---|
| 6,787,357 B2 | 9/2004 | Bowlin et al. |
| 6,790,455 B2 | 9/2004 | Chu et al. |
| 6,790,528 B2 | 9/2004 | Wendorff et al. |
| 6,821,479 B1 | 11/2004 | Smith et al. |
| 2002/0090725 A1 | 7/2002 | Simpson et al. |
| 2004/0037813 A1 | 2/2004 | Simpson et al. |
| 2004/0166169 A1 | 8/2004 | Malaviya et al. |
| 2004/0191215 A1 | 9/2004 | Froix et al. |
| 2004/0229333 A1 | 11/2004 | Bowlin et al. |
| 2004/0258729 A1 | 12/2004 | Czernuszka et al. |

FOREIGN PATENT DOCUMENTS

| | | |
|---|---|---|
| WO | 2005121316 A1 | 12/2005 |

OTHER PUBLICATIONS

Hubbell, J.A. Biomaterials in tissue engineering. Biotechnology (NY) 1995; 13:565-576.

Myllyharju, J., et al. Collagens and collagen-related diseases. Ann Med. 2001; 33:7-21, Abstract only.

Nair, L.S., et al. Development of novel tissue engineering scaffolds via electrospinning. Expert Opin Biol Ther. 2004; 4:659-668, Abstract only.

Ogawa, K., et al. A sulphur matrix complex elastic fibril composed of a fine core of amorphous elastin and microfibrils was largely accumulated in the aortic intima of aged rats. J Electron Microsc (Tokyo) 2003; 52:175-82.

Willits, R.K., et al. Effect of collagen gel stiffness on neurite extension. J Biomater Sci Polym Ed. 2004; 15 (12):1521-31.

Desgranges, P., et al. Extracellular matrix covered biomaterials for human endothelial cell growth. Int J Artif Organs. 1992; 15(12):722-6, Abstract only.

Hodde, J.P., et al. Vascular endothelial growth factor in porcine-derived extracellular matrix. Endothelium. 2001; 8 (1):11-24, Abstract only.

Huang, L., et al. Engineered collagen-PEO nanofibers and fabrics. J Biomater Sci Polym Ed. 2001; 12(9):979-93.

Lacroix, H., et al. Early inflammatory response to gelatin- and collagen-sealed Dacron prostheses. Ann Vasc Surg 1995; 9: 152-154, Abstract only.

Nikolaychik, V.V., et al. A new method for continual quantitation of viable cells on endothelialized polyurethanes. J. Biomater Sci Polym Ed 1996; 7:881-891, Abstract only.

Nikolaychik, V.V., et al. In vitro testing of endothelial cell monolayers under dynamic conditions inside a beating ventricular prosthesis. ASAIO J 1996; 42: M487-M494, Abstract only.

Bidez, P.R. III, et al. Polyaniline, an electroactive polymer, supports adhesion and proliferation of cardiac myoblasts. J Biomater Sci Polym Ed 2006; 17(1/2): 199-212.

Stankus, J.J., et al. Fabrication of biodegradable elastomeric scaffolds with sub-micron morphologies. J Biomed Mater Res. 2004; 70A(4): 603-14.

Bhattarai, S.R., et al. Novel biodegradable electrospun membrane: Scaffold for tissue engineering. Biomaterials 2004; 25:2595-2602.

Boland, E.D., et al. Electrospinning collagen and elastin: Preliminary vascular tissue engineering. Front Biosci. 2004; 9:1422-1432.

Buchko, C.J., et al. Processing and microstructural characterization of porous biocompatible protein polymer thin films. Polymer 1999; 40:7397-7407.

Garcia, A.J. Get a grip: Integrins in cell-biomaterial interactions. Biomaterials. 2005; 26:7525-7529.

Croce, M.A., et al. Adhesion and proliferation of human dermal fibroblasts on collagen matrix. J Biomater Appl, 2004; 18:209-222.

Eble, J.A., et al. Rhodocetin antagonizes stromal tumor invasion in vitro and other alpha2beta1 integrin-mediated cell functions. Matrix Biol. 2002; 21:547-558.

Solomon, D.E. An in vitro examination of an extracellular matrix scaffold for use in wound healing. Int J Exp Pathol 2002; 83:209-216.

Huang, Z.M., et al. A review on polymer nanofibers by electrospinning and their applications in nanocomposites. Compos Sci and Technol. 2003; 63:2223-2253.

Zhao, F., et al. Effects of hydroxyapatite in 3-D chitosan-gelatin polymer network on human mesenchymal stem cell construct development. Biomaterials 2006; 27: 1859-1867.

Jokinen, J., et al. Integrin-mediated cell adhesion to type I collagen fibrils. J. Biol. Chem. 2004; 279:31956-31963.

Carvalho, R.S., et al. Selective adhesion of osteoblastic cells to different integrin ligands induces osteopontin gene expression. Matrix Biol 2003; 22: 241-249.

Kim, K, et al. Control of degradation rate and hydrophilicity in electrospun non-woven poly(D, L-lactide) nanofiber scaffolds for biomedical applications. Biomaterials 2003; 24:4977-4985.

Kozel, B.A., et. al. Deposition of tropoelastin into the extracellular matrix requires a competent elastic fiber scaffold but not live cells. Matrix Biol. 2004; 23:23-34.

Li, M., et al. Electrospun Blends of Natural and Synthetic Polymers as Scaffolds for Tissue Engineering. School of Biomedical Engineering, Science and Health Systems, Drexel University, USA. Presented on Apr. 26, 2005 for Drexel Research Day.

Li, M., et al. Electrospun protein fibers as matrices for tissue engineering. Biomaterials 2005; 26:5999-6008.

Perets, A., et al. Novel Natural Scaffolds from Matrigel for Diverse Tissue Engineering Applications. School of Biomedical Engineering, Science and Health Systems, Drexel University, USA. Presented on Apr. 26, 2005 for Drexel Research Day.

Li, W.J. et al. Electrospun nanofibrous structure: A novel scaffold for tissue engineering. J. Biomed Mater Res. 2002; 60:613-621.

Lu, Q., et al. Novel porous aortic elastin and collagen scaffolds for tissue engineering. Biomaterials. 2004; 25 (22):5227-5237.

Blasi, P., et al. Plasticizing effect of water on poly(lactide-co-glycolide). J Controlled Release 2005; 108: 1-9.

Min, B.M., et al. Electrospinning of silk fibroin nanofibers and its effect on the adhesion and spreading of normal human keratinocytes and fibroblasts in vitro. Biomaterials 2004; 25:1289-1297.

Vacanti, J.P., et al. Transplantation of cells in matrices for tissue regeneration. Adv. Drug Deliv. Rev. 1998; 33:165-182.

Mo, X.M., et al. Electrospun P(LLA-CL) nanofiber: A biomimetic extracellular matrix for smooth muscle cell and endothelial cell proliferation. Biomaterials. 2004; 25: 1883-1890.

Ntayi, C., et al. Elastin-derived peptides upregulate matrix metalloproteinase-2 mediated melanoma cell invasion through elastin-binding protein. J. Invest Dermatol. 2004; 122:256-265.

Prockop, D.J.,et al. Collagens: molecular biology, diseases, and potentials for therapy. Annu Rev Biochem. 1995; 64:403-34.

Shin, M., et al. Contractile cardiac grafts using a novel nanofibrous mesh. Biomaterials. 2004; 25(17):3717-3723.

Toshima, M., et al. Three-dimensional architecture of elastin and collagen fiber networks in the human and rat lung. Arch Histol Cytol. 2004; 67:31-40.

Xu, C.Y., et al. Aligned biodegradable nanofibrous structure: A potential scaffold for blood vessel engineering. Biomaterials. 2004; 25:877-886.

Yoshimoto, H., et al. A biodegradable nanofiber scaffold by electrospinning and its potential for bone tissue engineering. Biomaterials 2003; 24:2077-2082.

Stitzel, J. Controlled fabrication of a biological vascular substitute. Biomaterials 2006; 27:1088-1094.

Bhattarai, N., et al. Electrospun chitosan-based nanofibers and their cellular compatibility. Biomaterials 2005; 26:6176-6184.

Buttafoco, L., et al. Electrospinning of collagen and elastin for tissue engineering applications. Biomaterials 2006; 27:724-734.

Li, M. Electrospinning polyaniline-contained gelatin nanofibers for tissue engineering applications. Biomaterials 2006; 27:2705-2715.

Mondrinos, M.J., et al. Engineering three-dimensional pulmonary tissue constructs. Tissue Eng. 2006; 12(4): 717-728.

Brannon-Peppas, L. Polymers in controlled drug delivery. Medical Plastics and Biomaterials. Nov. 1997; 34.

Wagers, et al. Little evidence for developmental plasticity of adult hematopoietic stem cells. Science. 2002; 297: 2256-2259.

Zhang, Y., et al. Electrospinning of gelatin fibers and gelatin/PCL composite fibrous scaffolds. J Biomed Mater Res. Sep. 22, 2004.

Faury, G. Function-structure relationship of elastic arteries in evolution: from microfibrils to elastin and elastic fibres. Pathol Biol (Paris). 2001; 49:310-25.

Li, S., et al. Biochemistry and biomechanics of cell motility. Annu Rev Biomed Eng 2005; 7: 105-150.

Katti, D.S., et al. Bioresorbable nanofiber-based systems for wound healing and drug delivery: Optimization of fabrication parameters. J. Biomed Mater Res. 2004; 70:286-296.

Kim, B.S., et al. Scaffolds for engineering smooth muscle under cyclic mechanical strain conditions. J Biomech Eng. 2000; 122:210-215.

Wu, L., et al. Effects of porosity and pore size on in vitro degradation of three-dimensional porous poly(D,L-lactide-co-glycolide) scaffolds for tissue engineering. J Biomed Mater Res A 2005; 75: 767-777.

Li, W.J., et al. Biological response of chondrocytes cultured in three-dimensional nanofibrous poly(epsilon-caprolactone) scaffolds. J. Biomed Mater Res. 2003; 67:1105-1114.

Luu, Y.K., et al. Development of a nanostructured DNA delivery scaffold via electrospinning of PLGA and PLA-PEG block copolymers. J. Control Release. 2003; 89(2):341-53.

Hench, L.L. Third-generation biomedical materials. Science 2002; 295:1014-1017.

Kwon, I.K. Co-electrospun nanofiber fabrics of poly (L-lactide-co-epsilon-caprolactone) with type I collagen or heparin. Biomacromolecules 2005; 6: 2096-2105.

Shin, M., et al., In vivo bone tissue engineering using mesenchymal stem cells on a novel electrospun nanofibrous scaffold. Tissue Eng. 2004; 10(1-2):33-41.

Stankus, J.J., et al. Fabrication of biodegradable elastomeric scaffolds with sub-micron morphologies. J Biomed Mater Res. 2004; 70A(4): 603-14.

Xu, C., et al. Electrospun nanofiber fabrication as synthetic extracellular matrix and its potential for vascular tissue engineering. Tissue Eng. 2004; 10(7-8):1160-8.

Bokel, C., et al. Integrins in development: Moving on, responding to, and sticking to the extracellular matrix. Dev Cell 2002; 3: 311-321.

Matthews, J.A., et al. Electrospinning of collagen nanofibers. Biomacromolecules. 2002; 3(2): 232-8.

Radisic, M., et al. High-density seeding of myocyte cells for cardiac tissue engineering. Biotechnol Bioeng. 2003; 82(4): 403-14.

Levenberg, S., et al. Differentiation of human embryonic stem cells on three-dimensional polymer scaffolds. Proc Natl Acad Sci USA. 2003; 100(22):12741-6.

Sheu, M.T., et al. Characterization of collagen gel solutions and collagen matrices for cell culture. Biomaterials. 2001; 22(13):1713-9.

Long, J.L., et al. Elastic fiber production in cardiovascular tissue-equivalents. Matrix Biol. 2003; 22(4):339-50.

Yang, F., et al. Electrospinning of nano/micro scale poly(L-lactic acid) aligned fibers and their potential in neural tissue engineering. Biomaterials. 2005; 26(15):2603-10.

Combelles, C.M., et al. In vitro maturation of human oocytes and cumulus cells using a co-culture three-dimensional collagen gel system. Hum Reprod. 2005: 20(5): 1349-1358.

McClure et al. "Electrospun Polydioxanone, Elastin, and Collagen Vascular Scaffolds: Uniaxial Cyclic Distension" 2009, Journal of Engineered Fibers and Fabrics 4(2):18-25.

McClure et al., "Cross-linking Electrospun Polydioxanone-Soluble Elastin Blends: Material Characterization," 2008 Journal of Engineered Fibers and Fabrics 3(1):1-10.

Sell et al., "Cross-linking methods of electrospun fibrinogen scaffolds for tissue engineering applications," 2008, Biomed.Mater 3(4):045001.

Smith, et al., "Suture-reinforced electrospun polydioxanone-elastin small-diameter tubes for use in vascular tissue engineering: a feasibility study." 2008, Acta Biomaterialia 4:58-66.

* cited by examiner

ELECTROSPUN BLENDS OF NATURAL AND SYNTHETIC POLYMER FIBERS AS TISSUE ENGINEERING SCAFFOLDS

BACKGROUND OF THE INVENTION

1. Field of Invention

This invention relates to engineering of functional three-dimensional (3-D) tissue constructs for the replacement and/or repair of damaged native tissues.

2. Description of Related Art

Engineering of functional three-dimensional (3-D) tissue constructs for the replacement and/or repair of damaged native tissues using cells and scaffolds is one of the ultimate goals of tissue engineering. The following references describe various scaffolds:

Zhang Y, Ouyang H, Lim C T, Ramakrishna S, Huang Z M., Electrospinning of gelatin fibers and gelatin/PCL composite fibrous scaffolds, J Biomed Mater Res. 2004 Sep. 22;

Xu C, Inai R, Kotaki M, Ramakrishna S., Electrospun nanofiber fabrication as synthetic extracellular matrix and its potential for vascular tissue engineering. Tissue Eng. 2004 July-August; 10 (7-8):1160-8; and Stankus J J, Guan J, Wagner W R., Fabrication of biodegradable elastomeric scaffolds with sub-micron morphologies. J Biomed Mater Res. 2004 Sep. 15; 70A(4): 603-14.

Further information regarding scaffolds can be obtained from U.S. Pat. Nos. 6,306,424, 6,616,435, 6,689,166, 6,753,311, 6,790,455, 6,790,528 and 6,821,479 and U.S. Patent Application Publication No. 2002/0090725 to Simpson et al.

Problems with currently available scaffolds include the following: current scaffold need to be crosslinked, mechanical properties are not suitable for multiple applications, and limited cell in-growth.

Accordingly, there is a need in the art to provide scaffolds with better mechanical properties and improved cell in-growth capabilities.

All references cited herein are incorporated herein by reference in their entireties.

BRIEF SUMMARY OF THE INVENTION

The invention provides fibers and nanofibrous biocompatible biomatrices electrospun from a blend of synthetic polymers, such as PLGA and natural proteins, especially containing elastin, can be used as tissue engineering scaffolds and implanted into the body to replace/repair damaged/non-functional tissues. These particular blends provide a unique mix of mechanical and physical properties that facilitates cell penetration and proliferation within the scaffolds without crosslinking.

Inventors have observed that the fibrous scaffolds made from the blend remain intact in complete cell culture medium with serum for over one month without crosslinking. In addition, the fiber-gel structure creates a fibrous matrix that is malleable and allows migration of cells throughout the scaffold.

In this invention, non-woven fibrous scaffolds were electrospun from a tertiary blend of the synthetic biodegradable polymer such as, for example, poly(lactic-co-glycolic acid) (PLGA) and natural proteins, such as, for example, gelatin (denatured collagen) and elastin. The electrospinning process is attractive for fabrication of scaffolds for tissue engineering due to the simplicity of system set-up and ability to generate nanoscale features. In addition, the electrospinning process is capable of generating fibrous scaffolds from both natural and synthetic polymers. The limitation of scaffolds fabricated using the electrospinning process is the high fiber density and the resultant "fish net effect". In other words, fiber density in electrospun mats is often too high to allow for ingrowth of cells. Possible solutions include the use of composite scaffolds containing heterogeneous fibers that display different solubility in a given solvent to create "spacers". The major drawback of fibrous protein scaffolds is the need for crosslinking in order to prevent rapid hydrolysis of the fibers. In order to create composite scaffolds that do not require crosslinking and display enhanced capacity to support the 3-D tissue assembly, the present invention offers a solution to this problem by using a tertiary blend fibers of polymers and natural fibers such as PLGA, gelatin, and elastin.

The initial plan was to use co-spinning (each material in different syringe) of PLGA and natural proteins such as collagen without crosslinking, so that when the scaffold was placed into aqueous medium the non-crosslinked protein fibers would dissolve, producing a porous PLGA fiber mesh. This approach seemed interesting, however, inventors decided to try dissolving multiple materials in the same solution to see if this would produce an even more porous scaffold. To investigate this possibility, mixed spinning (all materials in the same solution) of a tertiary blend of PLGA, gelatin, and elastin was carried out. Unexpectedly, the resultant fiber mat became a solid fiber-gel composite upon placement into aqueous medium, rather than the non-crosslinked components completely dissolving. The PGE mats were visibly swollen in aqueous medium and had a gel-like appearance, although it was clear that there were still solid fiber components in the scaffold. Furthermore, seeding of PGE scaffolds with bone marrow stromal cells resulted in contraction of PGE scaffolds to <50% of the original swollen size.

Electrospinning provides an efficient approach to fabricating biomimetic scaffolds from both natural and synthetic polymer and proteins for tissue engineering. Inventors electrospun a fibrous composite PGE scaffold composed of PLGA, gelatin, and elastin. The advantage of this scaffold was the beneficial characteristics of each individual component synergizing to form a composite with more superior three dimensional cell culture properties. This conclusion is corroborated by histological analyses indicating that rBMSCs attach, migrate, and proliferate within the PGE matrix, resulting in extremely high cell densities by 4 weeks of in vitro culture. These scaffolds would have wide applicability in a number of tissue engineering systems due to their ability to support dense cell growth, thus having the ability to deliver extremely high cell numbers. This novel approach to generating composite scaffolds of natural and synthetic biomaterials affords tissue engineers the ability to meet all necessary design criteria in fabricating scaffolds for a given application.

The invention will be described using poly(lactic-co-glycolic acid)-gelatin-elastin fibers (PGE) as a non-limiting example. In the absence of a cross-linking agent, the average PGE fiber diameter increased from 347±103 nm to 999±123 nm upon wetting as measured by scanning electron microscopy. Rat bone marrow stromal cells (rBMSC) were used paradigmatically to study the 3-D cell culture properties of PGE scaffolds. Consistent with the observed properties of the individual fibers, PGE scaffolds initially swelled in aqueous culture medium, however rBMSC seeded PGE scaffolds contracted to <50% of original size. Time course histological analysis demonstrated uniform seeding of rBMSC into PGE scaffolds and complete cell penetration into the fibrous architecture over 4 weeks of in vitro culture.

Accordingly, the invention includes a fiber comprising an electroprocessed blend of at least one synthetic polymer and at least two natural polymers without crosslinking, wherein one of the at least two natural polymers is elastin or a pro-form of elastin or an elastin-like materials.

In certain embodiments, one of the at least two natural polymers is gelatin.

In certain embodiments, said synthetic polymer is at least one of poly (epsilon-caprolactone) (PCL), poly (lactic acid) (PLA), poly (glycolic acid) (PGA), and the copolymers poly (lactide-co-glycolide) (PLGA) or polyaniline.

In certain embodiments, said electroprocessed blend is an electrospun blend.

In certain embodiments, said electrospun blend comprises said synthetic polymer, denatured collagen and elastin at a ratio of 3:1:2 (v/v/v).

In certain embodiments, said electrospun blend comprises said synthetic polymer, denatured collagen and elastin at a ratio of 2:2:2 (v/v/v).

Another object of the present invention is to provide a scaffold made from the fiber as described above.

In certain embodiments, the scaffold further comprises a cell. In certain embodiments, the scaffold further comprises a pharmaceutical agent.

A further object of the present invention is to provide a method of making a fiber as described above, the method comprising providing a blend of at least one synthetic polymer and at least two natural polymers without crosslinking, wherein one of the at least two natural polymers is elastin or a pro-form of elastin or an elastin-like materials; and electroprocessing the blend to form the fiber. In certain embodiments, said electroprocessing is electrospinning.

Yet another object of the present invention is to provide a method of using a scaffold, the method comprising contacting the scaffold with a cell.

In certain embodiments, the fiber comprises a pharmaceutical agent.

In certain embodiments, collagen is excluded from the fiber.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Extracellular matrix proteins are important modulators of the cellular microenvironment, making them attractive choices for the fabrication of tissue-engineered scaffolds [1-3].

Engineered scaffolds made solely out of these proteins provide some measure of functionality and elasticity [3,12,13]. Fabrication of collagen and elastin scaffolds using the electrospinning process requires chemical cross-linking in order to prevent hydrogel transition and eventual dissolving of the fibers in aqueous medium (28). This chemical cross-linking facilitates mechanical stability of the fibers in aqueous medium, but not without it's drawbacks. The fibers become rigid and resistant to cell penetration and certainly lose some degree of biological activity due to cross-linking of amino acid residues. Collagen hydrogels allow for uniform cell growth throughout the 3-D architecture and maintain integrin mediated adhesions (30). however hydrogel scaffolds lack the mechanical properties required. The mechanical properties of these ECM protein hydrogel scaffolds can be enhanced using synthetic, biodegradable polymers, such as poly(lactic-co-glycolic acid) (PLGA). We hypothesize that electrospinning of natural and synthetic polymers dissolved in the same solution without subsequent cross-linking of the protein components would allow for the formation of a stable fiber-hydrogel composite upon introduction into aqueous medium.

In the present invention, electrospinning is a preferred form of electroprocessing. The term "electroprocessing" shall be defined broadly to include all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. "Electrospinning" means a process in which fibers are formed from a solution or melt by streaming an electrically charged solution or melt through an orifice. "Electroaerosoling" means a process in which droplets are formed from a solution or melt by streaming an electrically charged polymer solution or melt through an orifice. The term electroprocessing is not limited to the specific examples set forth herein, and it includes any means of using an electrical field for depositing a material on a target.

Electrospinning is an attractive process for fabricating scaffolds for tissue engineering applications due to the simplicity of the process and the ability to generate microscale and nanoscale features with synthetic and natural polymers [14, 28]. To date, a broad range of polymers has be processed by electrospinning, including polyamides, polylactides, cellulose derivatives, water soluble polymers such as polyethyleneoxide, as well as polymer blends or polymers containing solid nanoparticles or functional small molecules [15]. More recently the electrospinning process has been employed for producing fibrous scaffolds for tissue engineering from both natural and synthetic polymers [16]. Bowland et al. fabricated a three-layered vascular construct by electrospinning collagen and elastin [17]. To date, electrospun fibrous scaffolds have been fabricated with numerous synthetic biodegradable polymers, such as poly($\in$-caprolactone) (PCL), poly(lactic acid) (PLA), poly(glycolic acid) (PGA), and the copolymers poly(lactide-co-glycolide) (PLGA) [18-21]. Electrospun scaffolds have been proposed for use in the engineering of bone tissue [22-24] and cardiac grafts [25]. Similarly, poly (L-lactide-co-$\in$-caprolactone) [P(LLA-CL)] has been electrospun into nanofibrous scaffolds for engineering blood vessel substitutes [26,27].

Any solvent can be used that allows delivery of the material or substance to the orifice, tip of a syringe, or other site from which the material will be electroprocessed. The solvent may be used for dissolving or suspending the material or the substance to be electroprocessed. Solvents useful for dissolving or suspending a material or a substance depend on the material or substance. Electrospinning techniques often require more specific solvent conditions. For example, collagen can be electrodeposited as a solution or suspension in water, 2,2,2-trifluoroethanol, 1,1,1,3,3,3-hexafluoro-2-propanol (also known as hexafluoroisopropanol or HFIP), or combinations thereof. Fibrin monomer can be electrodeposited or electrospun from solvents such as urea, monochloroacetic acid, water, 2,2,2-trifluoroethanol, HFIP, or combinations thereof. Elastin can be electrodeposited as a solution or suspension in water, 2,2,2-trifluoroethanol, isopropanol, HFIP, or combinations thereof, such as isopropanol and water. In one desirable embodiment, elastin is electrospun from a solution of 70% isopropanol and 30% water containing 250 mg/ml of elastin. Other lower order alcohols, especially halogenated alcohols, may be used. Other solvents that may be used or combined with other solvents in electroprocessing natural matrix materials include acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone.

One limitation of electrospun scaffolds fabricated with single materials is the high fiber density and the resultant fishnet effect, with the fiber density in electrospun mats is often too high to allow for ingrowth of cells. A major drawback of fibrous protein scaffolds is the need for crosslinking in order to prevent rapid hydrolysis of the delicate fibers. Possible solutions include the use of composite scaffolds containing heterogeneous fibers of natural and synthetic origin which display differential gel-solid state transition upon introduction to aqueous medium in order to create fiber-hydrogel composites. With that, the solid state synthetic polymer material can function as a fibrous backbone while non-crosslinked protein hydrogel components act as promoters of cellular attachment and growth. In this invention, PLGA, gelatin and elastin were dissolved in the same HFP solvent and electrospun this mix into a 3-D fibrous mat. Upon exposure to aqueous medium the resultant composite PGE scaffold became a stable fiber-laden hydrogel with suitable mechanical properties without need for chemical cross-linking. Furthermore, PGE scaffolds displayed superior capacity to support 3-D tissue-like assembly when compared to fiber scaffolds constructed from the individual components. Thus, this novel composite scaffold exhibited some of the advantages of the individual components, providing proof of concept for the engineering design principles.

Synthetic polymers of the invention include biodegradable and non-biodegradable polymers. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolid-es) (PLGA), polyanhydrides, and polyorthoesters or any other similar synthetic polymers that may be developed that are biologically compatible. The term "biologically compatible, synthetic polymers" shall also include copolymers and blends, and any other combinations of the forgoing either together or with other polymers generally. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated by reference as if set forth fully herein.

Examples of natural polymers of the invention include, but are not limited to, amino acids, peptides, denatured peptides such as gelatin from denatured collagen, polypeptides, proteins, carbohydrates, lipids, nucleic acids, glycoproteins, minerals, lipoproteins, glycolipids, glycosaminoglycans, and proteoglycans. In certain embodiments, collagen is excluded.

Pharmaceutical agents suitable herein can be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules.

Pharmaceutical agents include any therapeutic molecule including, without limitation, any pharmaceutical substance or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, anti-thrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Material and Methods

Materials

Gelatin (bovine skin, type B powder), alpha-elastin (soluble bovine, lyophilized powder) were purchased from Sigma (St Louis Mo.). Poly(lactide-co-glycolide) (PLGA) 90/10 was synthesized according to and processed into porous foams. In brief: The mixture chloroform solution of PLGA and sugar (10~15 wt % and 90~85 wt % respectively) was cast in a glass dish and put it in air for removal of the chloroform, and then it is put into water to dissolve the sugar. The biodegradation of PLGA in 90/10 is about 6 month. Unless noted otherwise all chemicals and reagents, including 1,1,1,3,3,3 Hexafluoro-2-Propanol (HFP) and Chloroform (CHCl3) were purchased from Sigma-Aldrich.

Purifying PLGA

PLGA 90/10 foam was added to in a large amount of chloroform with shaking at RT until fully dissolved. Then the PLGA solution was filtered through a glass microfibre filter (GF/A, circle 55 mm Ø, Whatman®) with vacuum assistance. Finally, PLGA was dried in the chemical hood by overnight evaporating all chloroform at RT. Final concentration: ~30 wt %=300 mg/ml in HFP (30% P-H).

Final Solution: Mix approximately 1 ml 30% P-H, 0.7 ml 8.3% gelatin, 1.3 ml 20% elastin together. Stir w/ heating the solution in water bath for about 30 min.

Electrospinning

Electrospinning was carried out as follows: polymer materials (PLGA, gelatin and alpha-elastin) were dissolved in HFP at concentrations of 30%, 8% and 20% (w/v), respectively, and then mixed as a blend PGE solution (in HFP) at the ratio of 2:3:5 (v/v/v). The blend solution was loaded into 5 ml plastic syringes (from Becton Dickinson, BD) equipped with blunt 18 gauge needles. The syringes were then placed in a syringe pump (14-831-1, KD Scientific Single-Syringe Infusion Pump, from Fisher) and the needles connected to the positive output of a high voltage power supply (ES30-0.1P, Gamma High Voltage Research, Inc.). Fibers were electrospun onto a grounded brass plate (25 mm×75 mm). The solution delivery rate was set at 1.5 ml/h. Electrospinning was carried out with the high voltage power supply set at 10 kV and an air gap distance of 15 cm.

Scanning Electron Microscopy

For analysis of this PGE constructs, scaffolds were sputter-coated with Au/Pd and examined with a scanning electron microscope (SEM, XL-30 Environmental SEM-FEG). Each micrograph from an SEM scan was digitized. The average fiber diameter was calculated using UTHSCSA ImageTool 3.0 software.

Microtensile Test

The tensile properties of electrospun 3-D fibrous protein scaffolds, approximately 0.2-0.5 mm×5 mm×50 mm (H×W×L), were characterized in a Kawabata Evaluation System (KES-G1, Kato Tech Co., Japan) using routine mechanical testing methods for fabric materials. The specimens were mounted vertically on two 1×1 cm mechanical gripping units of the tensile tester, leaving a 40 mm gauge length for mechanical loading. A strain rate of 0.2 mm/sec, sensitivity of 5×10 (10 V=1000 grams), and frequency of 50 Hz were used in the tensile tests.

Scaffold Sterilization

PGE scaffolds were sterilized overnight by soaking in 10% antibiotic containing phosphate buffer saline (PBS) followed by a short exposure to UV light (10 minutes on each side). The scaffolds were then washed with PBS 3 times vigorously to remove residual antibiotic, followed by several washes with serum-free Dulbecco's Modified Eagle's Medium (DMEM) to condition the surface for cell attachment.

Cell Seeding

The PGE scaffolds (5×5×0.25 mm) were placed in a 100 mm Petri dishes on an orbital shaker and seeded overnight using a 500,000/mL suspension of rat bone marrow stromal cells (rBMSC) in complete cell culture medium (see below). PGE scaffolds were seeded using a 500 K/mL suspension of bone marrow stromal cells (BMSCs) overnight on the Belly Dancer. As mentioned earlier, the PGE scaffolds contracted to <50% of their size prior to seeding during the ~16 hr seeding process.

Cell Culture rBMSCs (a gift of Dr. Itzhak Fischer, Department of Neurobiology and Anatomy, DUCOM) were maintained essentially as previously reported (33). Briefly, a 50/50 mixture of alpha-MEM and Ham's F-12 media containing 10% FBS and antiobiotics was used. The BMSCseeded PGE constructs were cultured under static conditions at 37° C. in a 5% $CO_2$ for up to 28 days, with samples taken at 24 hours, 7 days, and 28 days to evaluate cell in-growth over an extended in vitro culture period.

Extended Culture

BMSCs are maintained in a 50/50 mixture of alpha-MEM and Ham's F-12 media containing 10% FBS and antiobiotics. In these experiments the BMSC-seeded PGE constructs were cultured under static conditions for up to 28 days, with samples taken at 24 hours, 7 days, and 28 days. It would have been desirable to have more time points between 7 and 28 days, however there were limited samples and it was decided to let the samples go for ~1 month to look at cell ingrowth over an extended in vitro culture period.

Histological Characterization

At 24 hours, 7 days, and 28 days PGE constructs were harvested and fixed in 10% formalin for 1-2 hours at room temperature, followed by overnight fixation at 4° C. The next morning the samples were washed with PBS several times and stored in PBS until embedding and sectioning. The PGE constructs were embedded in OCT compound (Tissue-Tek), frozen at −20° C., and sectioned using the Reichert 1800 cryostat.

Results and Discussion

Electrospun PGE Scaffold

Figure 1A:
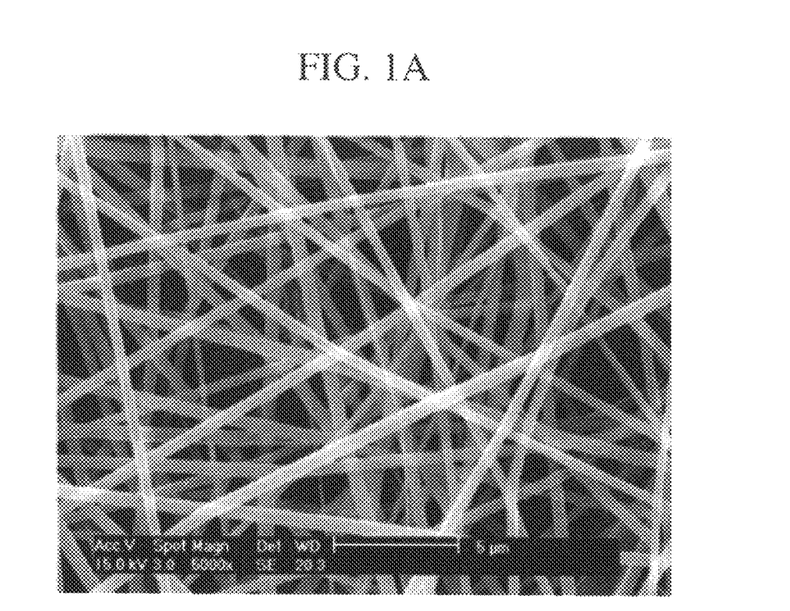
FIG. 1A shows a SEM photograph of PGE scaffold before it was soaked in double distilled (dd) $H_2O$.
Figure 1B:
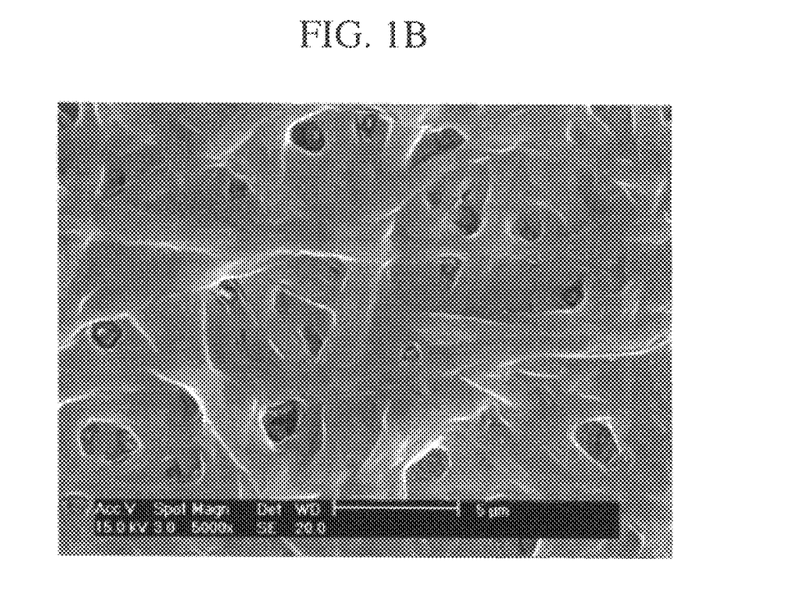
FIG. 1B shows a SEM photograph of PGE scaffold after it was soaked in dd $H_2O$.
Figure 2:
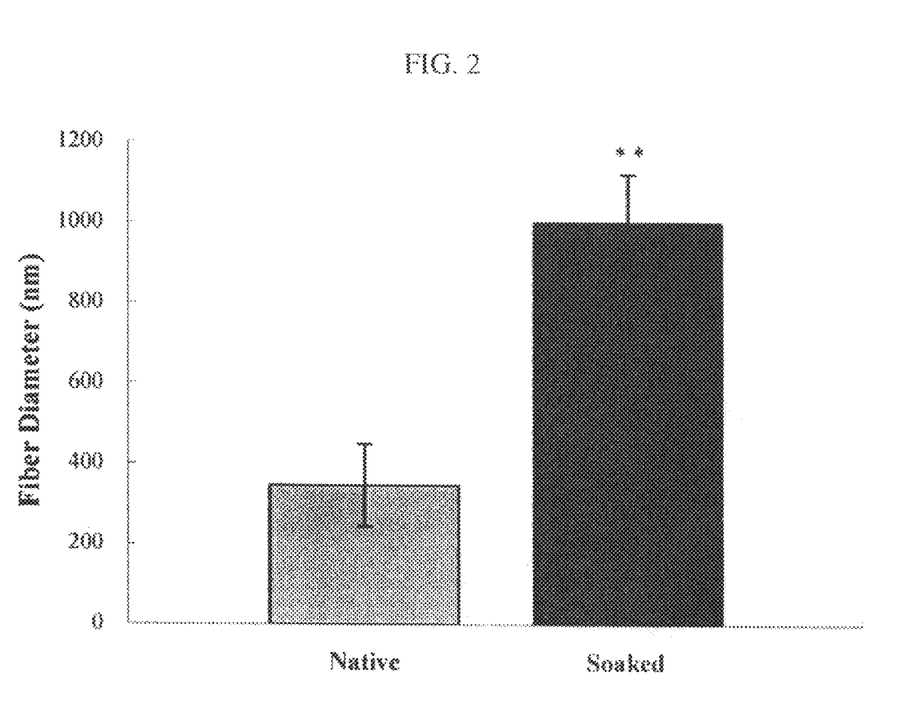
FIG. 2 shows a bar graph depicting fiber sizes of PGE scaffold before and after being soaked in water.

Based on our previous studies on electrospinning parameters [28], PGE was electrospun into mats approximately 0.5 mm thick at 10 kV and 1.5 ml/h flow rate with 15 cm air gap distance. Resultant PGE fibers were homogenous in appearance (FIG. 1A), suggesting that the PGE fibers are hybrid fibers composed of PLGA, gelatin, and elastin, rather than a mixture of homogeneous PLGA, gelatin, and elastin fibers. This observation is in stark contrast to previous reports. Boland et al. who report heterogeneous/phase separated deposition of co-spun elastin and collagen fibers. In our experiments, the average fiber diameter of PGE was 347±103 nm (n=30). The diameter of homogeneous PLGA fibers was 372±112 nm, gelatin was 349±97 nm, and elastin was 605±102 nm at the same electrospinning condition, which indicated that the fiber sizes did not change significantly with co-electrospinning. To test the behavior of electrospun PGE scaffolds in an aqueous environment, the fibrous mats were soaked for 1 h in distilled water. PGE scaffolds swelled, resembling an opaque hydrogel and becoming more three dimensional than the fibrous mats obtained following electrospinning. SEM images, taken after drying the soaked PGE mats clearly indicated swelling of the fibers (see FIG. 1(B)). The average diameter of soaked PGE fibers is 999±123 nm (n=10), which is much larger than the native PGE fibers (p<0.01) (FIG. 2). Swelling of electrospun fibers and formation of fiber-hydrogel composites, specifically of tertiary blends of synthetic biodegradable polymers and natural extracellular matrix proteins has never been reported. While not wishing to be bound by a specific theory for this behavior, inventors propose that the blend PGE is arranged in such a way that PLGA serves as a backbone while the water-soluble ECM molecules gelatin/elastin are arranged, facing the aqueous phase adsorbed on it.

Microtensile Properties of PGE Scaffolds

Figure 3A:
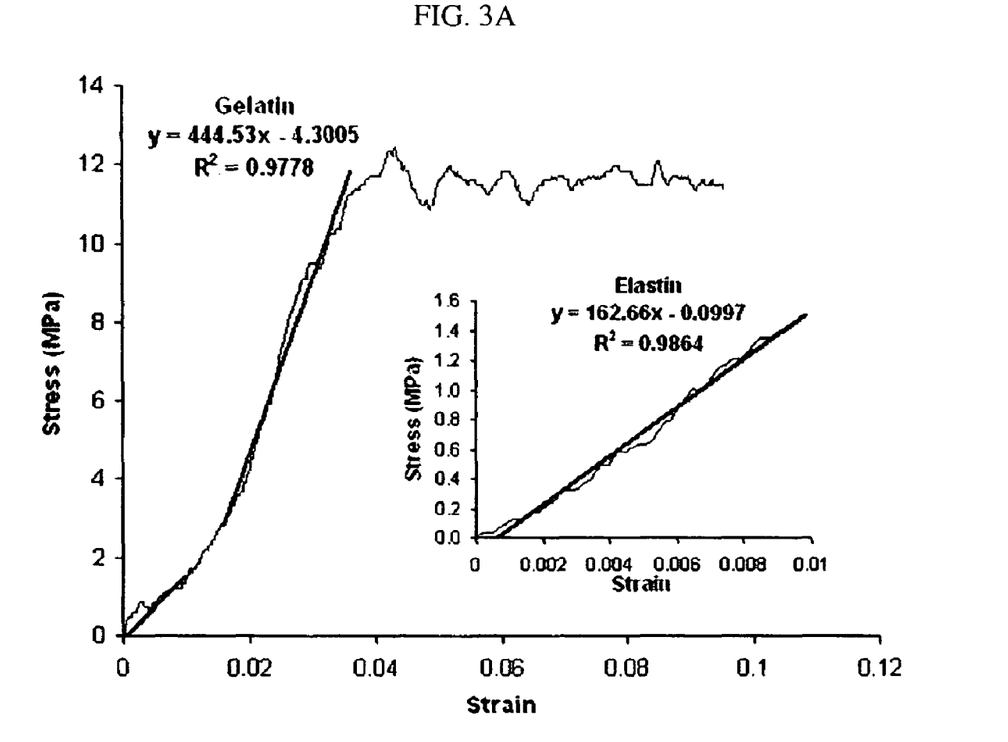
FIG. 3A is a graph depicting tensile properties of electrospun gelatin and elastin.
Figure 3B:
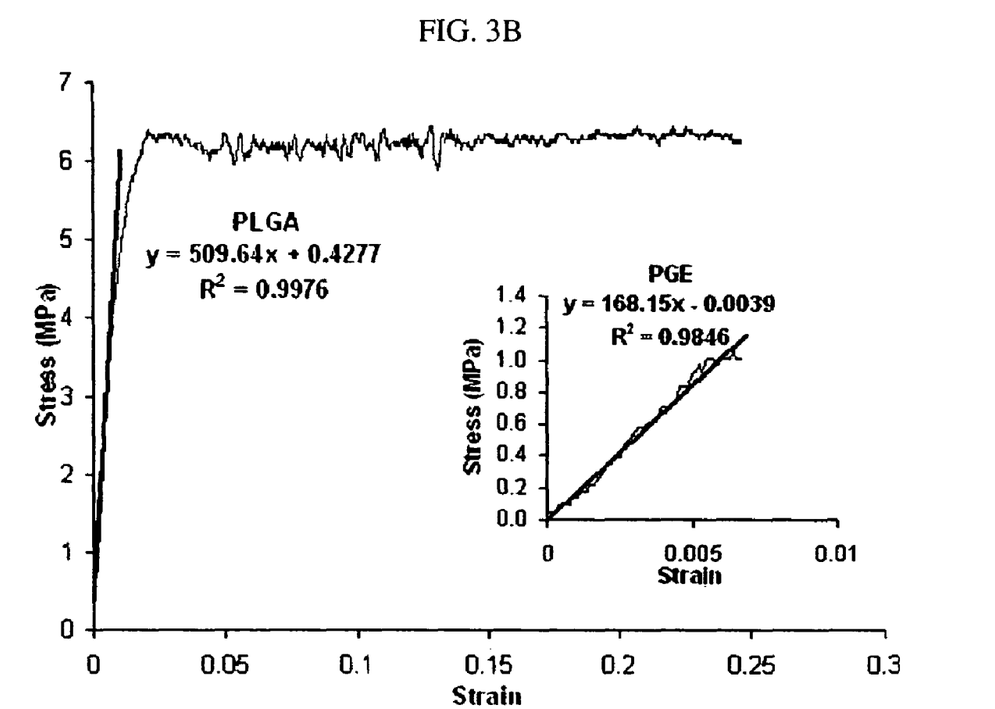
FIG. 3B is a graph depicting tensile properties of electrospun PLGA and PGE scaffolds.

Inventors compared the mechanical properties of non-cross linked dry fibrous mats prepared from respectively: 8% gelatin, 20% elastin, 30% PLGA, and PGE, using a microtensile tester. As seen in FIGS. 3A-3B, the secondary tensile moduli are about 445 MPa for gelatin and 510 MPa for PLGA, while the modulus of elastin is smaller, 162 MPa. By comparison, the tensile property of PGE scaffold is 168 MPa, essentially the same as that of elastin.

Cell Growth in PGE Scaffolds

After overnight seeding of rBMSC into PGE scaffolds on an orbital shaker, PGE constructs were transferred to fresh cell culture plate and cultured for a period of 4 weeks. Upon seeding with rBMSC, the PGE scaffolds contracted to <50% of the original swollen size. Histological characterization of the PGE constructs indicated BMSCs uniformly and efficiently penetrated into the scaffolds following the approximately 16 hour seeding period. Histological images of the constructs at 24 hours, 7 days, and 4 weeks postseeding demonstrated that rBMSCs penetrated into the fibrous scaffold after only 24 hours seeding and continued to proliferate over time as evidenced by increasing cell densities in histological sections.

Discussion

Inventors provided data characterizing the structural and mechanical properties and 3-D cell culture applicability of a novel composite fibrous scaffold composed of PLGA, gelatin, and elastin. PLGA is a gold standard biomaterial that has seen wide applications in tissue engineering and drug delivery confirming superior biocompatibility as compared with most synthetic polymers. For this reason, PLGA was selected as the synthetic component of engineered matrix of the invention.

In addition, inventors believe that the synthetic polymer components of such composite matrices, in this case PLGA, could be used as a delivery vehicle for proteins (21) or DNA (29) as needed to facilitate the molecular events needed for generation of given tissue. Structural proteins such as gelatin and elastin fibrils are an important factor for the mechanical properties of the ECM as well as for or cell attachment and migration. The fibrous morphology of the collagenous and elastic components of the ECM in various organs has been well characterized (6). In an attempt to mimic these properties, our fibrous scaffolds are engineered to be porous, pliable, and elastic, so that cells will be able to integrate and/or push the ECM-like fibers aside as they grow into the scaffolds. This design aim was realized, as evidenced by the formation of a fiber-hydrogel composite with mechanical properties similar to homogeneous elastin that allowed for cell penetration while retaining gross physical properties that would be required for eventual transplantation of constructs generated in vitro.

The finding that PGE matrices have secondary tensile moduli essentially identical to homogeneous elastin is surprising given the fact that the blend contains approx. 2/5 (v/v) of 20% PLGA and 8% gelatin combined and 3/5 (v/v) of 20% elastin. This high contribution of the low tensile modulus of elastin may explain the superior cell growth characteristics, in that the cells can easily penetrate the scaffolds. The swelling and hydrogel formation within the PGE matrix upon exposure to aqueous medium is in our opinion what facilitates the superior tissue-like assembly observed within these matrices after 28 days of in vitro culture the interior of the scaffold contains large cell numbers. These images demonstrate complete penetration of cells with high density throughout the cross-section of an electrospun fiber scaffold. Remarkably, there is no evidence of a necrotic core as is often seen in attempts to engineer macroscopic tissue constructs in vitro, indicating that the porosity of the scaffold might facilitate transport of nutrient into the scaffold and removal of toxic waste. We surmise that the robust cellular penetration observed in the absence of overt necrosis is due to the malleability of the PGE matrix.

This scaffold design is a prototype for future composites that will combine the benefits of engineered synthetic materials and natural extracellular matrix proteins.

The results of these experiments are very exciting in that they demonstrate complete cell penetration of electrospun fiber scaffolds. Such high cell density throughout the cross-section of an electrospun fiber scaffold has not been reported to the best of our knowledge. The major problem with the PGE scaffolds is that we have not been able to reproduce the material properties observed in the first batch. Possible reasons include the use of a different type of PLGA (the PGE described here was fabricated with PLGA (from China) and the more recently fabricated PGE was made with PLGA from Absorbable Polymers, Inc.). PGE fabricated since the original batch do not display the swelling properties upon placement in aqueous medium, nor do they contract when seeded with BMSCs. These scaffolds would have wide applicability in a number of tissue engineering systems due to their ability to support dense cell growth, thus having the ability to deliver extremely high cell numbers.

The invention will be illustrated in more detail with reference to the following Examples, but it should be understood that the present invention is not deemed to be limited thereto.

EXAMPLES

Example 1

In this Example, composite scaffolds composed of synthetic and natural materials with physicochemical properties suitable for tissue engineering applications are described. Fibrous scaffolds were co-electrospun from a blend of a synthetic biodegradable polymer (poly-(lactic-co-glycolic acid), PLGA, 10% solution) and two natural proteins, gelatin (denatured collagen, 8% solution) and α-elastin (20% solution) at ratios of 3:1:2 and 2:2:2 (v/v/v). The resulting PLGA-gelatin-elastin (PGE) fibers were homogeneous in appearance with an average diameter of 380±80 nm, which was considerably smaller than fibers made under identical conditions from the starting materials (PLGA: 780±200 nm; gelatin: 447±123 nm; elastin: 1060±170 nm). Upon hydration, PGE fibers swelled to an average fiber diameter of 963±132 nm, but did not disintegrate. Importantly, PGE scaffolds were stable in an aqueous environment without crosslinking and were more elastic than those made of pure elastin fibers. In order to investigate the cytocompatibility of PGE, we cultured H9c2 rat cardiac myoblasts and rat bone marrow stromal cells (BMSCs) on fibrous PGE scaffolds. We found that myoblasts grew equally as well or slightly better on the scaffolds than on tissue-culture plastic. Microscopic evaluation confirmed that myoblasts reached confluence on the scaffold surfaces while simultaneously growing into the scaffolds. Histological characterization of the PGE constructs indicated that BMSCs penetrated into the center of scaffolds and began proliferating shortly after seeding. Our results suggest that fibrous scaffolds made of PGE and similar biomimetic blends of natural and synthetic polymers may be useful for engineering soft tissues, such as heart, lung and blood vessels.

Under these conditions, the solid state synthetic polymer material may function as a fibrous backbone while the associated, non-crosslinked protein components act as promoters of cellular attachment and growth. In this study, we dissolved PLGA, gelatin and elastin in the same solvent (1,1,1,3,3,3 Hexafluoro-2-Propanol, HFP) and electrospun this tertiary blend into fibrous matrices. Upon exposure to aqueous medium the resultant composite PGE scaffold turned into stable fiber-laden hydrogel with suitable mechanical properties without need for chemical crosslinking. Furthermore, PGE scaffolds displayed an enhanced capacity to support 3-D tissue-like assembly when compared to fibrous scaffolds constructed from the individual components. This novel composite scaffold exhibited advantages beyond those of the individual components, providing the proof-of-concept for tailoring scaffolds for specific tissue engineering purposes.

Materials and Methods

Materials: Gelatin (bovine skin, type B powder, catalog no. G9391), alpha-elastin (soluble bovine, lyophilized powder, catalog no. E6527) were purchased from Sigma (St Louis, Mo.). Poly (lactide-co-glycolide) (PLGA) 90/10 was synthesized and characterized at the Changchun Institute of Applied Chemistry, Chinese Academy of Sciences, P. R. China. The biodegradation of 90/10 PLGA is about 6 months. Unless otherwise noted, all chemicals and reagents, including 1,1,1,3,3,3 Hexafluoro-2-Propanol (HFP), were purchased from Sigma-Aldrich.

Electrospinning: Electrospinning was carried out as previously described. 12 In brief: PLGA, gelatin and alpha-elastin were dissolved in HFP at concentrations of 10%, 8% and 20% (w/v), respectively, and then mixed as a blend PGE solution (in HFP) at the ratio of 3:1:2 and 2:2:2 (v/v/v), abbreviated by PGE 312 and PGE 222, respectively. The blend solutions were loaded into 3 ml plastic syringes (from Becton Dickinson, BD) equipped with blunt 18 gauge needles. The syringes were then placed in a syringe pump (14-831-1, KD Scientific Single-Syringe Infusion Pump, from Fisher) and the needles connected to the positive output of a high voltage power supply (ES30-0.1P, Gamma High Voltage Research, Inc.). Fibers were electrospun onto a grounded brass plate (25 mm×75 mm) or 15 mm glass coverslips (Fisher). The solution delivery rate was set at 1.5 ml/h. Electrospinning was carried out with the high voltage power supply set at 10 kV and an air gap distance of 12 cm. For cell culture studies the mats were sterilized by exposure on both sides for one hour each to a conventional ultraviolet (UV) source (30 Watts, 65 cm working distance) in the laminar-flow hood. UV treatment did not result in crosslinking, as assessed by the fact that the fiber morphology in UV-sterilized test mats composed of elastin and/or gelatin fibers was indistinguishable from that of non-treated mats. Moreover, the UV-sterilized elastin and/or gelatin mats dissolved in an aqueous environment, just as did the non-treated ones.

TABLE

Composition of PGE blend fibers

| Sample | PLGA (HFP) Solution | Gelatin (HFP) Solution | Elastin (HFP) Solution | Solution ratio(v:v:v) |
|---|---|---|---|---|
| PGE10 | 10% (w/v) | 8% (w/v) | 20% (w/v) | 2:1:1 |
| PGE15 | 15% (w/v) | 8% (w/v) | 20% (w/v) | 2:1:1 |
| PGE20 | 20% (w/v) | 8% (w/v) | 20% (w/v) | 2:1:1 |
| PGE312 | 10% (w/v) | 8% (w/v) | 20% (w/v) | 3:1:2 |
| PGE222 | 10% (w/v) | 8% (w/v) | 20% (w/v) | 2:2:2 |

Table Average Diameter of PGE blend fibers

| Sample | PGE10 | PGE15 | PGE20 |
|---|---|---|---|
| Diameter (um) | 0.695 ± 0.175 | 0.951 ± 0.258 | 1.938 ± 0.216 |

Microtensile Test: The tensile properties of electrospun fibrous PGE and PLGA mats, approximately 0.2-0.5 mm–5 mm×50 mm (H×W×L), were characterized in a Kawabata Evaluation System (KES-G1, Kato Tech Co., Japan) using routine mechanical testing methods for fabric materials. Dry samples were measured after electrospinning and wet samples were measured after soaking samples in ddH2O for 1 hour for thorough wetting. The specimens were mounted vertically on two 1×1 cm mechanical gripping units of the tensile tester, leaving a 15 mm gauge length for mechanical loading. The load cell size was 1 kg (10 Newton), loading resolution was 50 g/V, and the spatial resolution was 0.01 mm. The strain rate used was 0.08/second. In the text, strain ($\Delta L/L$) is a dimensionless parameter, defined as the ratio of the changed length ($\Delta L$) following stress divided by the original length of the sample (L).

Cell Culture and Seeding:

H9c2 rat myoblasts (ATCC CRL-1446; American Type Culture Collection, Rockville, Md., USA) were used for studying cell attachment and proliferation on PGE and PLGA fiber-coated coverslips. H9c2 cells were grown in Dulbecco's Modified Eagle's Medium (DMEM) with 4.5 g/L glucose supplemented with 4 mM L-glutamine, 25 IU/mL penicillin and 25 µg/mL streptomycin (diluted from stock concentrations of 5,000 IU/mLl penicillin and 5,000 ug/mL streptomycin, Cellgro, Herndon, V A), and 10% fetal bovine serum (FBS, Hyclone, Logan, Utah) under standard culture conditions (37° C., 5% CO2), as we previously described.

Neonatal rat bone marrow stromal cells (BMSC), a kind gift from Dr. Itzhak Fischer, Drexel University College of Medicine, were maintained in a 50/50 mixture of alpha-MEM and Ham's F-12 media containing 25 IU/mL penicillin and 25 µg/mL streptomycin, and 10% FBS. We used BMSCs in addition to H9c2 cells in order to (a) validate our findings with more than one cell type and (b) assess the penetration of the cells into the scaffolds by histology (shown below). For the seeding experiments, PGE and PLGA fibers were electrospun as 100-150 µm thick "coatings" on circular 15 mm glass coverslips. These PGE-coated coverslips were sterilized by exposure to UV light for 2 hours on each side before cell seeding, and then secured in 24-well culture plates using Viton O-rings (Cole-Parmer). PGE-coated coverslips were seeded with H9c2 cells as described below in section 2.6. In addition, BMSC were seeded into the 3-D scaffolds, as described below in section 2.7.

Microscopic Analysis: For analyzing the fibrous constructs by SEM, dry scaffolds were sputter-coated with platinum (Pt) and examined with a scanning electron microscope (SEM, XL-30 Environmental SEM-FEG). SEM images of hydrated samples were taken and the fiber dimensions determined after air-drying the samples at room temperature (RT) overnight or, for fast drying, baking them on a hot plate (70-80 degree C., 2-5 minutes). Each micrograph from an SEM scan was digitized. For each sample, the average fiber diameter was calculated from at least 30 randomly selected fibers in SEM micrographs.

For cytological assessment, samples were fixed in 10% buffered formalin for 1 hour at RT and then left overnight in PBS at 4° C. The samples were washed once with 1×PBS, and the cells permeabilized for 15 minutes in 0.2% Triton-X 100 (Sigma) in PBS (Cellgro). Following a gentle wash in PBS, the samples were incubated for 15 minutes in PBS containing 2 µg/mL Hoechst 33258 (Bis-benzimide, Sigma, catalog no. B1155), a nuclear stain, and 1 µg/mL rhodamine-phalloidin (Phalloidin-tetramethylrhodamine B isothiocyanate, Sigma, catalog no. P1951), a specific stain for microfilaments. Samples were visualized on a Leica DMRX upright microscope equipped with the appropriate fluorescence filters. Digital images were acquired using a Leica D C 300FX camera.

To assess the ultrastructure of H9c2 cells cultured on PGE and PLGA fibers, samples were fixed with 2.5% glutaraldehyde for 1 hour at RT and then left overnight in PBS at 4° C. The samples were washed with PBS and then dehydrated in graded ethanol,15%, 30%, 50%, 70%, 85%, 95%, and 100% (twice), for 10 minutes each followed by drying in a critical point dryer (CPD, SPI CPD 7501, West Chester, Pa.), as previously described.36,37 The samples were then sputter-coated with Pt, and visualized by SEM as above.

Attachment and Proliferation Assay: Cell attachment to and proliferation on the scaffolds were tested using H9c2 rat cardiac myoblasts and measured with a continual fluorescence assay (AlamarBlue™ [AB], Biosource, Alameda, Calif.), as previously reported. H9c2 cells were seeded onto the PGE and PLGA fiber-coated coverslips, control glass coverslips and TCPS surfaces at a density of 10,000 cells/well. Following overnight attachment in complete DMEM in a tissue culture incubator, supernatants were removed and 1.5 ml fresh complete DMEM containing 5% (v/v) AB was added into each well. After 4 hours incubation, triplicate 100 μl aliquots of the AB-containing medium were removed from each well for fluorescence measurement. Subsequently the AB-containing medium in the wells was replaced with fresh complete medium without AB. AlamarBlue™ fluorescence in the samples was determined as previously described. 12 For continual assessment of cell proliferation, the AB assay was performed on the same cell population every other day for up to 8 days until the cells reached confluence. The data was normalized for each well to the initial AB fluorescence readings at day 0 (the first AB reading taken 12-18 hours post-plating).

Characterization of Cells on and in 3-D PGE Scaffolds: The PGE scaffolds (5×5×0.25 mm) were placed in a 100 mm Petri dish on an orbital shaker (Belly Dancer™, Stovall, setting 6) and seeded overnight using a 500,000/mL suspension of either H9c2 myoblasts or BMSCs in cell culture medium. As indicated in the results section, samples were harvested at various time points and processed for either scanning electron microscopy (SEM) or routine histology. For SEM the samples were fixed in 2.5% glutaradehyde, first for 1 h at RT followed by overnight fixation at 4 degree C. Samples were processed by dehydration in graded ethanol, followed by critical point drying (CPD), as previously described.36,37 For histological characterization, PGE constructs were harvested at 24 hours and 7 days. The samples were fixed in 10% formalin for 1 h at RT, followed by overnight fixation at 4 degree C. The next morning, fixed PGE constructs were washed with PBS several times and stored in PBS until further processing. The PGE constructs were embedded in Tissue Freezing Medium (Fisher Scientific, catalog no. 15-183-38), frozen at −20° C., and sectioned using the Reichert 1800 cryostat. Cryosections, 10 μm thickness, were stained routinely with hematoxylin and eosin (H&E) as previously described.

Statistical Analysis: Where applicable, all data are expressed as mean +/−standard deviation. Student's t-test and single factor ANOVA were used for parameter estimation and hypothesis testing, with $p<0.05$ and $p<0.01$ considered as being statistically significant and extremely significant, respectively.

Results and Discussion
Co-electrospun PGE Fibers

Based on data from the literature and our previous studies defining some critical electrospinning parameters for natural polymers. PGE and PLGA were electrospun into mats approximately 0.2-0.5 mm thick as described in Materials and Methods. Unless specified otherwise, studies were carried out using PGE 312 fibers as the representative blend. Resultant PGE fibers were homogenous, in appearance), and smaller than PLGA fibers. In our experiments, the average fiber diameter of PGE was 380+/−79 nm, which is statistically significantly smaller than pure PLGA fibers, 778+/−202 nm ($p<0.01$). The diameter of gelatin fibers was 349+/−97 nm and elastin fibers was 605+/−102 nm under similar electrospinning conditions. Bookmark not defined. These results suggest that upon electrospinning a heterogeneous PGE blend yields hybrid fibers composed of a homogenous blend of PLGA, gelatin, and elastin, rather than a mixture of individual PLGA, gelatin, and elastin fibers. This observation is in contrast to previous reports by Boland et al. who report heterogeneous/phase separated deposition of co-spun elastin and collagen fibers. As inferred from the resulting fiber diameters, the size of PGE fibers is significantly smaller than that of elastin and PLGA fibers, and approximately same as that of gelatin fibers, which is remarkable, since in terms of the mass of the ingredients, gelatin is the smallest constituent component.

When placed in cell culture medium, PGE scaffolds, unlike other scaffolds made of natural biopolymers, did not disintegrate, even in the absence of crosslinking. In contrast to the dry fibrous mats the wet PGE scaffolds swelled, resembling a 3-D opaque hydrogel as also confirmed by SEM). The average diameter of soaked PGE fibers increased to 963+/−132 nm (n=30), which is ~2-3 times larger than the native PGE fibers ($p<0.01$).

It is well known that PLGA will not swell or disintegrate/hydrolyze during the relatively short (overnight) incubation in an aqueous environment. In these experiments, the appearance of PLGA fibers soaked for up to 8 days was unchanged and remained similar to that of dry fibers (data not shown). PLGA (90/10) used for these studies has a half life of about 6 months and did not degrade significantly during the incubation periods used. Swelling of electrospun PGE fibers and formation of hydrolysis-resistant fiber-hydrogel composites, specifically, of tertiary blends of synthetic biodegradable polymers and natural extracellular matrix proteins has not been reported before. To explain this behavior, we propose that the blend PGE is arranged in such a way that PLGA serves as a backbone with the water-soluble ECM molecules gelatin/elastin arranged facing the aqueous phase adsorbed on it. Current experiments are underway to test this hypothesis.

These results are unique and in contrast to a recent report by Stitzel et al, who also co-electrospun a tertiary blend of synthetic and natural polymers, viz. PLGA, collagen and elastin. Inventors surmise that the differences in our findings may primarily be due to the fact that Stitzel et al. used (a) collagen instead of gelatin and (b) a ratio of synthetic to natural polymers which is quite different from ours.

Prior to hydration, the ultrastructure of the PGE 222 and PGE 312 fibers was quite similar, indicating homogenous fibers for both blends. Upon hydration in either H2O or cell culture medium, both PGE 222 and PGE 312 mats were stable without the need for chemical crosslinking. However, ultra-structural examination by SEM showed somewhat different morphologies. For PGE 222, invenotrs noticed bundling and separation into tiny fibers, around 120±11 nm. In contrast, separation and bundling were less pronounced in PGE 312. The reason for this interesting difference most probably lies in the different volume fractions of PGLA in both blends. The data clearly indicate the crucial importance of choosing the proper ratios of synthetic and natural polymers for customtailoring engineered scaffolds. Experiments are underway to elaborate on these observations.

Microtensile Properties of Electrospun PGE Mats

Inventors compared the mechanical properties of non-cross linked fibrous PGE and PLGA mats under both dry and wet conditions, using a microtensile tester. As seen below, the secondary tensile moduli of dry PLGA, PGE 312, and PGE 222 are 504±67 MPa, 254±111 MPa, and 122±23 MPa, respectively. Pure PLGA fibers have a higher tensile modulus than that of either PGE blend; reducing the PLGA contents in the blends also leads to a decrease in the tensile modulus ($p<0.05$). The elasticity of the fiber mats is affected by the amount of PLGA component in the blend. Pure PLGA produces the most elastic scaffold, while reducing the amount of PLGA in the blend, results in a decrease in the elasticity of PGE fibers ($p<0.01$). These data suggest that the mechanical properties of pure gelatin and elastin fiber scaffolds can be enhanced by co-spinning with synthetic polymers, such as polylactic/polyglycolic acid (PLA/PGA), to more realistically mimic the mechanical characteristics of natural ECM, as also pointed out by Stizel et al. 14

Comparing the mechanical properties of dry and wet samples, tensile modulus and strain data indicate that wet fibrous mats, made of PGE 312 or PGE 222, are always significantly more elastic than the dry mats. For example, for PGE 312, the tensile modulus decreased from 254±111 MPa (dry) to 43±11 MPa (wet, $p<0.01$), and the maximum strain increased from 0.04±0.01 to 0.64±0.02 ($p<0.01$). For PGE 222, the tensile modulus decreased from 122±23 MPa (dry) to 12±4 MPa (wet, $p<0.01$), and the maximum strain increased from 0.03±0.01 to 0.60±0.09 ($p<0.01$). These data indicate a ~20-fold increase in the elasticity of both PGE mats upon hydration. In contrast, hydration did not significantly affect the elasticity of PLGA mats. Measuring tensile properties of wet samples is physiologically more relevant, because when using these mats as tissue engineering scaffolds, cells react with wet fibers in an aqueous environment. These mechanical tests clearly indicate that PGE fibers represent a novel composite material with physicochemical properties unique and dissimilar from those of each of the parental materials.

Cell Proliferation on PGE Mats

To study the in vitro cytocompatibility of the electrospun fibrous scaffolds, PGE 222, PGE 312, and PLGA fibers were electrospun onto 15 mm circular glass coverslips, UV-sterilized and mounted inside the wells of a regular 24-well plate, as described in section 2.4. H9c2 rat cardiac myoblasts were seeded at a density of 10,000 cells/well in triplicate and allowed to proliferate for up to 8 days on PGE 222, PGE 312, PLGA fiber coated coverslips, and tissue-culture treated polystyrene (TCPS) control surfaces. The cells proliferated similarly on all substrates during the 8 day culture period, albeit with some slight differences on day 8. At this time point, there were slightly more cells on the PGE 222 and PGE 312 fiber coated coverslips than on TCPS surface ($p<0.05$). This is an indication that the 3-D structure of the fibrous substrates facilitates higher cell densities than 2-D TCPS substrates. We conclude that all fibrous substrates are equally cytocompatible for H9c2 cells and support cell proliferation to a degree which is equal to, if not slightly higher than on conventional "gold-standards", such as tissue-culture treated polystyrene.

Morphology of Cells Growing on PGE Fiber-coated Coverslips

In order to assess the morphology and cytoskeletal architecture of H9c2 cells on the different fiber coated coverslips, H9c2 cells were seeded and cultured as described in Materials and Methods.

At 36 hours post-seeding, subconfluent H9c2 cells grown on PGE 222 were more spread out than the cells growing on PLGA fibers. Similar observations were also made for cells growing on PGE 312. Under these experimental conditions, H9c2 cells formed confluent monolayers within 8 days on both the PGE and PLGA fibrous substrates, however with some significant morphological differences. On the PLGA substrates, just like on TCPS, the cells formed "conventional", aligned 2-D monolayers, as seen by light microscopy. In contrast, on PGE fiber coated coverslips, the cells seem to form multilayered "sheets", as inferred from the fluorescence micrograph. SEM micrographs confirm this impression, showing an aligned monolayer on PLGA and overlapping of H9c2 cells in the different layers of the fibrous PGE matrix.

Cell Penetration into 3-D PGE Fibrous Scaffolds

In addition to culturing H9c2 cells on PGE fiber coated coverslips, we also investigated the growth and penetration of both cardiac H9c2 myoblasts and bone marrow stromal cells (BMSCs) into thicker 3-D PGE and PLGA fibrous scaffolds (5 mm×5 mm×0.5 mm). The scaffolds were seeded and cultured as described in section 2.4 and 2.6. SEM micrographs, taken after 4 days of culture, confirm that H9c2 cells were able to invade the 3-D PGE fibrous scaffolds while remaining on the surface of 3-D PLGA scaffolds.

For histological analysis, BMSCs were seeded onto the scaffolds on an orbital shaker overnight. BMSCs readily penetrated into the fibrous PGE scaffolds within the first 24 hours, where they continued to proliferate over a 7-day culture period. Both of these figures were taken at the center of the samples demonstrating cell penetration throughout the cross-section of electrospun PGE fiber scaffolds, even as early as 24 hours post-seeding.

We note that both H9c2 and BMSC easily penetrate into the PGE scaffolds. We also note the striking difference in the penetration behavior of H9c2 into PGE and PLGA. This latter observation cannot simply be explained by differences in the mechanical properties of the two kinds of scaffolds. The fiber sizes are quite similar (~780 nm [PLGA] vs.~960 nm [PGE]), while PLGA mats are actually more elastic than PGE scaffolds. The latter property would intuitively call for better penetration of the cells into the PLGA scaffold, yet the data show the opposite.

It is believed that the inclusion of natural polymers enhances the interaction of the cells with the scaffolds by engaging cell adhesion molecules such as integrins, which then permit the cells to exert/generate higher traction forces as required for cell motility. Integrin-mediated cell migration in the ECM is essential in tissue development in vivo and cell scaffold interactions in vitro. Another important issue relevant to cell migration into our PGE scaffolds is the ability of the cell to remodel natural ECM proteins for which they possess digestive enzymes. Therefore, we believe the pliability/elasticity of a fibrous ECM, the attachment ligands presented, and the ability of the cells to remodel their environment dynamically interplay to control cell migration in 3-D scaffolds. The interplay between mechanical properties, integrin-mediated adhesion, and ECM turnover in determining cell-scaffold interactions is currently under investigation in many laboratories, including ours.

In tissue engineering, any degradable scaffold is meant to serve as a provisional matrix, i.e., promoting cell adhesion, migration and proliferation until the cells secret and deposit their own ECM. In this context, our PGE blend contains gelatin, rather than type I collagen. Gelatin is frequently used as a substrate for growing endothelial cells, and also as an adhesive substrate that does not alter the native characteristics of stem cells. It is well known, that many of the integrinbinding sites of cell adhesion and differentiation found in collagen are still present in gelatin. In terms of their immunogenic properties, no difference was found in the inflammatory response of collagen or gelatin coated vascular grafts. In keeping with the concept of a provisional matrix, PLGA was chosen as a synthetic biodegradable polymer component that provides enhanced mechanical properties in the short term while degrading over time to allow for cellular invasion with deposition and remodeling of the extracellular matrix.

Structural proteins such as collagen/gelatin and elastin fibrils are an important factor for the mechanical properties of the ECM as well as for cell attachment and migration. The fibrous morphology of the collagenous and elastic components of the ECM in various organs has been well characterized.6 In an attempt to mimic these properties, our fibrous scaffolds are engineered to be pliable and elastic via incorporation of PLGA, while providing natural ECM proteins as adhesion ligands via incorporation of gelatin and elastin, so that cells will be able to integrate with and invade into the scaffolds. This design aim was realized, as evidenced by the formation of a fiber-hydrogel composite with mechanical properties similar to homogeneous elastin12 that allows for cell penetration while retaining gross physical properties that would be required for eventual transplantation of constructs generated in vitro.

Importantly for in vitro and in vivo applications, when placed in an aqueous environment, the fibrous scaffolds remain intact and acquire a high degree of elasticity in the absence of crosslinking agents. The lack of chemical crosslinking also preserves the chemical structure of the natural protein constituents, thus allowing for enhanced cell adhesion/migration as well as ECM turnover. The swelling and hydrogel formation of the PGE matrix upon exposure to aqueous medium is in our opinion what facilitates the rapid tissue-like assembly observed within these matrices.

These scaffolds synergistically combine the beneficial characteristics of each individual component to form a composite which is stable in an aqueous environment and, due to its superior mechanical/elastic properties as well as presentation of natural ECM protein adhesion ligands to the cells, facilitates attachment and migration into the 3-D scaffolds. It is believed that composite scaffolds of synthetic and natural polymers, such as the PGE scaffolds described here, will have wide applicability in a number of applications in engineering soft tissues, such as blood vessels, and cardiac or pulmonary tissues. Hence, this scaffold design may represent a prototype for future composites that will combine the benefits of engineered synthetic materials and natural extracellular matrix proteins.

Cell adhesion, morphology, growth, and proliferation on/in scaffolds mimicking the extracellular matrix are largely mediated by integrins. The subunit expression of integrins will vary among different materials, in a cell-specific manner. Differential integrin expressions of cells cultured on electrospun PGE and the starting materials, PLGA, gelatin, elastin, respectively will be further studied. Specifically, differential integrin expression of cells growing in 3-D scaffolds vs. those of cells grown on 2-D surfaces coated with a thin film will be assessed by western blots and immunohistochemistry.

Abbreviations
rBMSC: rat bone marrow stromal cells
DMEM: Dulbecco's Modified Eagle's Medium
ECM: extracellular matrix
HFP: 1,1,1,3,3,3 Hexafluoro-2-Propanol
PBS: phosphate buffer saline
PCL: poly(∈-caprolactone)
PGA: poly(glycolic acid)
PLA: poly(lactic acid)
PLGA: poly(lactic-co-glycolic acid)
P(LLA-CL): poly(L-lactide-co-∈-caprolactone)
SEM: scanning electron microscope

REFERENCES

1. Lu Q, Ganesan K, Simionescu D T, Vyavahare N R. Novel porous aortic elastin and collagen scaffolds for tissue engineering. Biomaterials. 2004, 25(22):5227-5237.
2. Buijtenhuijs P, Buttafoco L, Poot A A, Daamen W F, van Kuppevelt T H, Dijkstra P J, de Vos R A, Sterk L M, Geelkerken B R, Feijen J, Vermes I. Tissue engineering of blood vessels: characterization of smooth-muscle cells for culturing on collagen-and-elastin-based scaffolds. Biotechnol Appl Biochem. 2004, 39(Pt 2):141-149.
3. Kim B S, Mooney D J. Scaffolds for engineering smooth muscle under cyclic mechanical strain conditions. J Biomech Eng. 2000, 122(3):210-5.
4. Jokinen J, Dadu E, Nykvist P, Kapyla J, White D J, Ivaska J, Vehvilainen P, Reunanen H, Larjava H, Hakkinen L, and Heino J, Integrin-mediated Cell Adhesion to Type I Collagen Fibrils, J. Biol. Chem. 2004; 279:31956-31963.
5. Croce M A, Silvestri C, Guerra D, Camevali E, Boraldi F, Tiozzo R, and Parma B, Adhesion and Proliferation of Human Dermal Fibroblasts on Collagen Matrix, J Biomater Appl, 2004, 18:209-222.
6. Toshima M, Ohtani Y, Ohtani O. Three-dimensional architecture of elastin and collagen fiber networks in the human and rat lung. Arch Histol Cytol. 2004, 67(1):31-40.
7. Ntayi C, Labrousse A L, Debret R, Birembaut P, Bellon G, Antonicelli F, Hornebeck W, Bernard P. Elastin-derived peptides upregulate matrix metalloproteinase-2-mediated melanoma cell invasion through elastin-binding protein. J Invest Dermatol. 2004, 122(2):256-265.
8. Prockop D J, Kivirikko K I, Collagens: molecular biology, diseases, and potentials for therapy, Annu Rev Biochem. 1995, 64:403-34.
9. Myllyharju J, et al., Collagens and collagen-related diseases, Ann Med. 2001, 33:7-21.
10. Ogawa K, Sasaki F, A sulphur matrix complex, elastic fibril composed of a fine core of amorphous elastin and microfibrils was largely accumulated in the aortic intima of aged rats, J Electron Microsc (Tokyo) 2003, 52:175-82.
11. Park J B. Structure-property relationships of biological materials. In: Biomaterials Science and Engineering. New York: Plenum Press 1984, 187-222.
12. Kozel B A, Ciliberto C H, Mecham R P. Deposition of tropoelastin into the extracellular matrix requires a competent elastic fiber scaffold but not live cells. Matrix Biol. 2004 April; 23(1):23-34.
13. Faury G. Function-structure relationship of elastic arteries in evolution: from microfibrils to elastin and elastic fibres. Pathol Biol (Paris). 2001 May;49(4):310-25.
14. Nair L S, Bhattacharyya S, Laurencin C T. Development of novel tissue engineering scaffolds via electrospinning. Expert Opin Biol Ther. 2004, 4:659-68.
15. Huang Z M, Zhang Y Z, Kotaki M, Ramakrishna S. A review on polymer nanofibers by electrospinning and their applicartions in nanocomposites. Composites Science and Technology. 2003, 63:2223-2253.
16. Buchko C J, Chen L C, Shen Y, and Martin D C. Processing and microstructural characterization of porous biocompatible protein polymer thin films. Polymer 1999, 40: 7397-7407.

17. Boland E D, Matthews J A, Pawlowski K J, Simpson D G, Wnek G E, Bowlin G L. Electrospinning collagen and elastin: preliminary vascular tissue engineering. Front Biosci. 2004, 9:1422-1432.
18. Li W J, Laurencin C T, Caterson E J, Tuan R S, Ko F K. Electrospun nanofibrous structure: a novel scaffold for tissue engineering. J Biomed Mater Res. 2002, 60(4):613-621.
19. Kim K, Yu M, Zong X, Chiu J, Fang D, Seo Y S, Hsiao B S, Chu B, Hadjiargyrou M. Control of degradation rate and hydrophilicity in electrospun non-woven poly(D,L-lactide) nanofiber scaffolds for biomedical applications. Biomaterials 2003, 24:4977-4985.
20. Bhattarai S R, Bhattarai N, Yi H K, Hwang P H, Cha D I, Kim H Y. Novel biodegradable electrospun membrane: scaffold for tissue engineering. Biomaterials 2004, 25: 2595-2602.
21. Katti D S, Robinson K W, Ko F K, Laurencin C T. Bioresorbable nanofiber-based systems for wound healing and drug delivery: Optimization of fabrication parameters. J Biomed Mater Res. 2004, 70B(2):286-296.
22. Li W J, Danielson K G, Alexander P G, Tuan R S. Biological response of chondrocytes cultured in three-dimensional nanofibrous poly(epsilon-caprolactone) scaffolds. J Biomed Mater Res. 2003, 67A(4):1105-1114.
23. Yoshimoto H, Shin Y M, Terai H, Vacanti J P. A biodegradable nanofiber scaffold by electrospinning and its potential for bone tissue engineering. Biomaterials 2003, 24(12):2077-2082.
24. Shin M, Yoshimoto H, Vacanti J P. In vivo bone tissue engineering using mesenchymal stem cells on a novel electrospun nanofibrous scaffold. Tissue Eng. 2004, 10(1-2): 3341.
25. Shin M, Ishii O, Sueda T, Vacanti J P. Contractile cardiac grafts using a novel nanofibrous mesh. Biomaterials. 2004, 25(17):3717-3723.
26. Mo X M, Xu C Y, Kotaki M, Ramakrishna S. Electrospun P(LLA-CL) nanofiber: a biomimetic extracellular matrix for smooth muscle cell and endothelial cell proliferation. Biomaterials. 2004, 25(10):1883-1890.
27. Xu C Y, Inai R, Kotaki M, Ramakrishna S. Aligned biodegradable nanofibrous structure: a potential scaffold for blood vessel engineering. Biomaterials. 2004, 25(5):877-886.
28. Li M, Mondrinos M J, Gandhi M R, Ko F K, Weiss A S, and Lelkes P I, Electrospun Protein Fibers as Matrices for Tissue Engineering, manuscript in preparation.
29. Luu Y K, Kim K, Hsiao B S, Chu B, Hadjiargyrou M. Development of a nanostructured DNA delivery scaffold via electrospinning of PLGA and PLA-PEG block copolymers. *J Control Release*. 89(2):341-53, 2003.
30. Eble J A, Niland S, Dennes A, Schmidt-Hederich A, Bruckner P, Brunner G. Rhodocetin antagonizes stromal tumor invasion in vitro and other alpha2beta1 integrin-mediated cell functions. *Matrix Biol.* 21(7):547-58, 2002.

While the invention has been described in detail and with reference to specific examples thereof, it will be apparent to one skilled in the art that various changes and modifications can be made therein without departing from the spirit and scope thereof.

What is claimed is:

1. A fiber comprising an electrospun blend of at least one synthetic polymer and at least two natural polymers, wherein none of the polymers is crosslinked, wherein said synthetic polymer is poly (lactide-co-glycolide) (PLGA) and wherein the at least two natural polymers are elastin and gelatin, further wherein said electrospun blend comprises said synthetic polymer, gelatin and elastin at a ratio of 30:8:40.

2. A scaffold made from the fiber of claim 1.

3. The scaffold of claim 2, further comprising a cell.

4. The scaffold of claim 2, further comprising a pharmaceutical agent.

5. The fiber of claim 1, further comprising a pharmaceutical agent.

6. A method of making the fiber of claim 1, the method comprising the steps of:
(a) providing a blend of at least one synthetic polymer and at least two natural polymers, wherein none of the polymers is crosslinked, wherein said synthetic polymer is poly (lactide-co-glycolide) (PLGA) and wherein the at least two natural polymers are elastin and gelatin, further wherein said electrospun blend comprises said synthetic polymer, gelatin and elastin at a ratio of 30:8:40; and
(b) electrospinning the blend to form the fiber.

7. A fiber comprising an electrospun blend of at least one synthetic polymer and at least two natural polymers, wherein none of the polymers is crosslinked, wherein said synthetic polymer is poly (lactide-co-glycolide) (PLGA) and wherein the at least two natural polymers are elastin and gelatin, further wherein said electrospun blend comprises said synthetic polymer, gelatin and elastin at a ratio of 20:16:40.

8. A scaffold made from the fiber of claim 7.

9. The scaffold of claim 8, further comprising a cell.

10. The scaffold of claim 8, further comprising a pharmaceutical agent.

11. The fiber of claim 7, further comprising a pharmaceutical agent.

12. A method of making the fiber of claim 7, the method comprising the steps of:
(a) providing a blend of at least one synthetic polymer and at least two natural polymers, wherein none of the polymers is crosslinked, wherein said synthetic polymer is poly (lactide-co-glycolide) (PLGA) and wherein the at least two natural polymers are elastin and gelatin, further wherein said electrospun blend comprises said synthetic polymer, gelatin and elastin at a ratio of 20:16:40; and
(b) electrospinning the blend to form the fiber.

* * * * *